United States Patent
Brabec et al.

(12) 
(10) Patent No.: US 6,253,110 B1
(45) Date of Patent: Jun. 26, 2001

(54) METHOD FOR TISSUE STIMULATION AND FABRICATION OF LOW POLARIZATION IMPLANTABLE STIMULATION ELECTRODE

(75) Inventors: Scott J. Brabec, Elk River; Kenneth R. Brennen, Fridley; William J. Schindeldecker, Foreston; Stanten C. Spear, Shoreview; Roger E. Rugland, Anoka; Bruce C. Johnson, Loretto, all of MN (US)

(73) Assignee: Medtronic INC, Mpls, MN (US)

( * ) Notice: Subject to any disclaimer, the term of this patent is extended or adjusted under 35 U.S.C. 154(b) by 0 days.

(21) Appl. No.: 09/300,020

(22) Filed: Apr. 27, 1999

(51) Int. Cl.[7] ........................................ A61N 1/05
(52) U.S. Cl. ............................................. 607/116
(58) Field of Search .................... 607/116, 119, 607/120, 121, 122

(56) References Cited

U.S. PATENT DOCUMENTS

| | | |
|---|---|---|
| 4,280,514 | 7/1981 | MacGregor . |
| 4,502,492 | 3/1985 | Bornzin . |
| 4,506,680 | 3/1985 | Stokes . |
| 4,679,572 | 7/1987 | Baker, Jr. . |
| 4,735,205 | 4/1988 | Chachques et al. . |
| 4,934,049 | 6/1990 | Kiekhafer et al. . |
| 4,972,848 | 11/1990 | DiDomenico et al. . |
| 5,016,645 | 5/1991 | Williams et al. . |
| 5,071,351 | * 12/1991 | Green, Jr. et al. ............... 607/116 |
| 5,265,608 | 11/1993 | Lee et al. . |
| 5,282,844 | 2/1994 | Stokes et al. . |
| 5,397,343 | 3/1995 | Smits . |
| 5,545,207 | 8/1996 | Smits et al. . |
| 5,571,158 | 11/1996 | Bolz et al. . |
| 5,683,443 | 11/1997 | Munshi et al. . |

* cited by examiner

Primary Examiner—William E. Kamm
(74) Attorney, Agent, or Firm—Girma Wolde-Michael (57) ABSTRACT

A method of fabricating a stimulation electrode for use on an implantable lead, the lead and electrode so fabricated and a method of their use. The electrode is made by coating a conductive electrode member with a coating of a high surface area coating having micron or sub-micron surface features and after coating, plasma cleaning the electrode member. The electrode is coupled to an insulated conductor of an implantable lead and is employed to stimulate body tissue. The high surface area coating may be platinum black, ruthenium oxide, another metal oxide, a metal nitride or the like. Steroid may be applied to the electrode member after coating.

6 Claims, 7 Drawing Sheets

METHOD FOR TISSUE STIMULATION AND FABRICATION OF LOW POLARIZATION IMPLANTABLE STIMULATION ELECTRODE

BACKGROUND OF THE INVENTION

The present invention relates to implantable stimulation leads generally and more particularly to implantable stimulation leads having electrodes optimized reduce post pulse polarization.

Following delivery of a cardiac pacing pulse by an electrode, an after potential typically remains on the electrode which persists for a sufficient period of time thereafter to interfere with sensing of cardiac signals associated with tissue depolarization caused by the delivered pulse. This phenomenon has been addressed in a number of ways over the years, and quite a large variety of electrode coatings have been developed in an effort to reduce post pulse polarization effects. One of the most common approaches to reducing post pulse polarization is to provide a high surface area coating having micron or sub-micron size surface features, such as a porous sintered metallic coating as described in U.S. Pat. No. 4,280,514 issued to MacGregor, a metal oxide or nitride coating as described in U.S. Pat. No. 4,679,572 issued to Baker, U.S. Pat. No. 5,571,158 issued to Bolz et al. and U.S. Pat. No. 5,683,443 issued to Munshi et al., or a coating of platinum black, as described in U.S. Pat. No. 4,502,492 issued to Bornzin, U.S. Pat. No. 4,506,680 issued to Stokes and U.S. Pat. No. 5,282,844 also issued to Stokes, all of which patents are incorporated herein by reference in their entireties. As noted in the these patents, the provision of a high surface area coating does substantially lower post pulse polarization levels. However, as a practical matter, further reduction in post pulse polarization levels are still desirable.

SUMMARY OF THE INVENTION

The present invention is directed to further reducing the post pulse polarization levels of pacing electrodes provided with platinum black or other high surface area coatings. The inventors have determined that this may be accomplished by plasma cleaning the electrodes toward the end of the lead manufacturing process, following application of the high surface area coating to the electrode. In particular, in the context of electrodes as in the above cited Stokes patents which are provided with a platinum black coating and which have a steroid coating applied after assembly of the lead, the plasma cleaning process may optimally be undertaken immediately prior to the steroid application step. Testing performed by the inventors on electrodes having platinum black coatings has indicated that the plasma cleaning step produces substantial reductions in post pulse polarization levels. While the specific mechanism by which plasma cleaning produces an electrode having improved polarization characteristics has not been precisely demonstrated, it is believed by the inventors that the plasma cleaning process removes hydrophobic contaminants from the surface which improves the "wetability" of the coating, which in turn assists in dispersion of ionic species adjacent the electrode surface and the discharge of the accumulated polarization following delivery of the pacing pulse.

It is believed by the inventors that plasma cleaning the previously coated electrodes is beneficial in the context of any pacing electrode, including endocardial, myocardial and epicardial electrodes, and including both pacing cathodes and pacing anodes. The improved polarization characteristics of the electrodes so produced is believed particularly valuable in improving the operation of the "auto-capture" features now present in some implantable pacemakers, which attempt to sense the heart depolarization waveform following delivery of the pacing pulse, which depolarization waveform in many cases overlaps the voltage waveform associated with decay of the post pulse polarization.

While the plasma cleaning process as described in detail herein is specifically applied to leads having platinum black, titanium nitride and ruthenium oxide coatings, it is also believed by the inventors that the plasma cleaning process is beneficial in the context of other porous or high surface area coatings having micron or sub-micron surface features, for example, sputtered, sintered or otherwise produced porous metal, metal oxide or metal nitride coatings, including platinum, iridium, titanium, iridium oxide, tantalum oxide, iridium nitride and the like, as disclosed in the MacGregor, Baker, Bolz et al. and Munshi et al. patents incorporated by reference above. It is believed that the improved wetability imparted by plasma cleaning following application of these types of high surface area coatings will also provide for improvements in post pulse polarization characteristics.

DETAILED DESCRIPTION OF THE PREFERRED EMBODIMENTS

Figure 1:
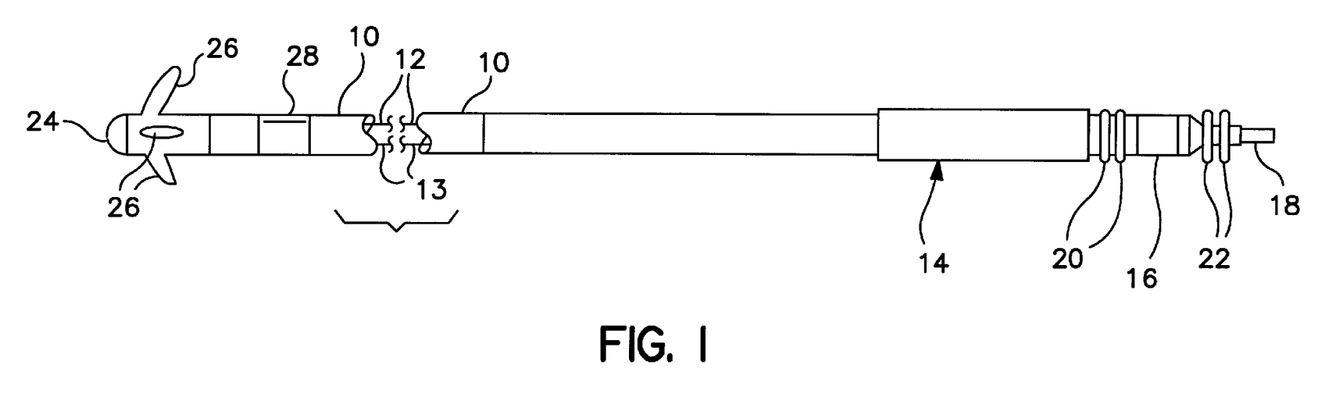
FIG. 1 is a plan view of a cardiac pacing lead of a type in which the present invention may usefully be practiced.

FIG. 1 is a plan view of one type of cardiac pacing lead in which the invention may usefully be practiced. In the case of FIG. 1, the lead is an endocardial pacing lead provided with an elongated insulative outer sheath 10 which carries two mutually insulated conductors 12 and 13, illustrated schematically. At the proximal end of the lead is an in-line bipolar connector assembly 14 which may correspond to the IS-1 connector standard. Connector assembly 14 is provided with a connector ring 16 coupled to conductor 12 and a connector pin 18 coupled to conductor 13. Sealing rings 20 and 22 are provided to seal the connector assembly within the bore of an associated cardiac pacemaker and to prevent fluid leakage between connector ring 16 and connector pin 18.

The proximal end of the lead carries a pacing cathode 24 and a pacing anode 28. Pacing cathode 24 may be any known type of pacing cathode employed in the context of cardiac pacing leads, however, it is illustrated as taking the general form of an endocardial pacing electrode. Tines 26 are optionally provided to assist in stabilizing electrode 24 adjacent heart tissue.

It should be understood in the context of the present invention that the lead of FIG. 1 is merely exemplary, and that the invention is believed useful in conjunction with any type of implantable stimulation lead, including epicardial pacing electrodes as described in U.S. Pat. No. 5,545,207 issued to Smits et al., myocardial electrodes as described in U.S. Pat. No. 5,397,343 issued to Smits, and defibrillation electrodes as described in U.S. Pat. No. 5,016,645 issued to Williams et al. and U.S. Pat. No. 4,934,049 issued to Kiekhafer et al., all of which are incorporated herein by reference in their entireties. The invention may also be useful in the field of muscle and nerve stimulation electrodes as disclosed in U.S. Pat. No. 4,735,205 issued to Chachques et al. and U.S. Pat. No. 5,265,608 issued to Lee et al., both of which are also incorporated herein by reference in their entireties. The provision of a platinum black or other high surface area coating having micron or sub-micron sized surface features, followed by a plasma cleaning process is believed to be beneficial in the context of all of these various electrode types.

Figure 2:
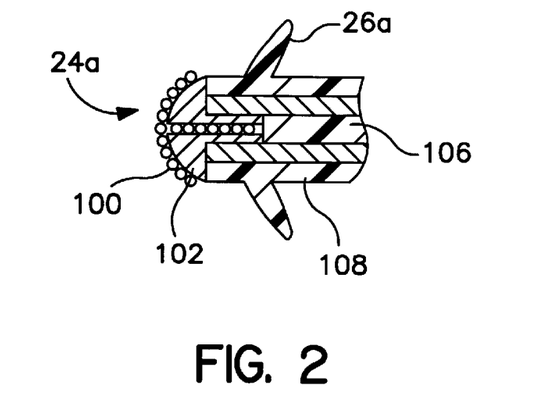
FIGS. 2, 3 and 4 are cross-sectional views through pacing cathodes having porous coatings, appropriate for use in practicing the present invention.

FIG. 2 is a cross-section through a first type of endocardial electrode appropriate for use in practicing the present invention. The electrode takes the form of a platinum electrode body 102 provided with a porous sintered coating of platinum particles 100 as described in the Stokes '680 patent cited above and thereafter coated with platinum black, for example using process described in the Bornzin '492 patent cited above. The lead is then assembled and the electrode is provided with a monolithic controlled release device 106 located within the shank 104. The electrode elutes steroid through the tubular passageway formed in the center of the electrode body and into contact with cardiac tissue. Also illustrated are optional tines 26a which assist in maintaining the electrode in contact with the endocardium, which tines are molded as part of a tine sheath 108. Following assembly of the lead, steroid is applied to the porous coating 100 of the electrode by dipping the electrode into a solution containing a steroid of the same general type as provided in the monolithic control device 106, and the lead is subsequently packaged. In the context of practicing the present invention, following assembly of the lead and prior to the steroid dip step, the electrode 24a would be cleaned by means of a plasma cleaner such as A Branson/IPC Model 4055/2 plasma etcher. During the plasma cleaning process, vacuum may be drawn down to 0.1 Torr, followed by inflow of an inert gas such as argon to produce a net pressure of 0.3 Torr. The electrode may then cleaned for 3 minutes at 300 watts and subsequently dipped in a steroid solution as described in the Stokes '680 patent cited above.

Figure 3:
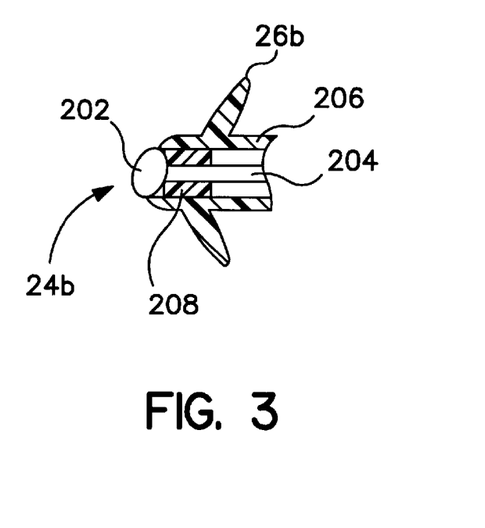

FIG. 3 is a cross-section through an alternative type of endocardial electrode in which the present invention may usefully be practiced. The electrode of FIG. 3 corresponds generally to that described in the above cited '844 Stokes patent, and includes an electrode 24b which is fabricated of a generally spherical porous sintered platinum electrode head 202 mounted to an elongated shaft 204 which is in turn coupled to a conductor within the lead. The lead is provided with a monolithic controlled release device 208 which is mounted around the shaft 204 and which elutes steroid through the porous electrode head 202 and into contact with body tissue. Optional tines 26b are provided mounted to a tine sleeve 206. As discussed in conjunction with the electrode of FIG. 2, the electrode is first fabricated and coated with platinum black and the lead is thereafter assembled to produce the structure illustrated in FIG. 3. The exposed portion of the electrode head 202 may then be plasma cleaned as discussed above in conjunction with FIG. 2, followed by application of a steroid coating to the electrode and packaging of the lead.

Figure 4:
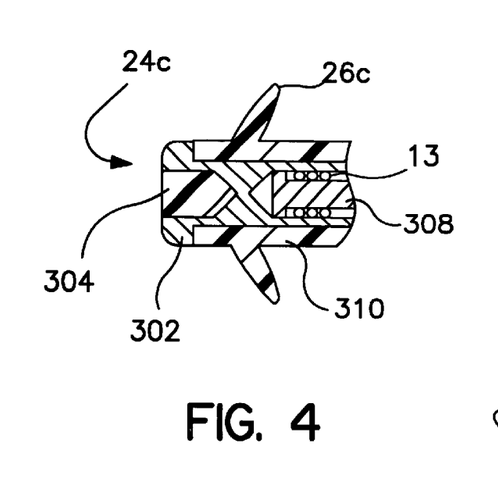

FIG. 4 is a cross-section through yet another alternative embodiment of an endocardial lead appropriate for use in practicing the present invention. In this case, the electrode 24c includes an exposed electrode portion 302 provided with a platinum black coating as described in the above cited Bornzin '492 patent. The electrode includes a distally facing bore in which a monolithic controlled release device 304 is mounted and a proximal extending electrode shank 304 which is coupled to an internal conductor 13 by means of a crimping core 308. Optional tines 26c are provided extending from a molded tine sleeve 310. In the context of the present invention, following assembly of the lead, the electrode may be cleaned according to the method set forth in conjunction with FIG. 2 and may optionally also have a coating of steroid applied thereto.

Figure 5:
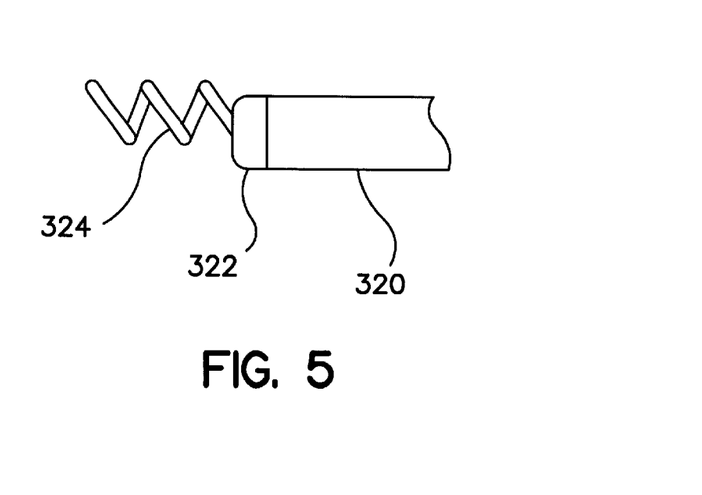
FIG. 5 is a surface view of the distal portion of a lead employing a helical electrode appropriate for use in practicing the present invention.

FIG. 5 is a plan view of the distal portion of a lead employing a helical electrode, appropriate for use in practicing the invention. Such leads typically employ an advancable helical electrode 324 which may be advanced or retracted from a molded electrode head at 320 and, in the context of the present invention may be provided with a coating of platinum black. End cap 322 may serve to enclose a monolithic controlled release device containing an anti-inflammatory steroid. The structure of such a lead is illustrated in more detail in U.S. Pat. No. 4,972,848, issued to Doan et al, and incorporated herein by reference in its entirety. In the context of the present invention, electrode 324 is preferably coated with a platinum black coating as described in the above cited Bornzin et al. patent, subsequently plasma cleaned, and thereafter optionally provided with a coating of an anti-inflammatory steroid prior to packaging.

Figure 6:
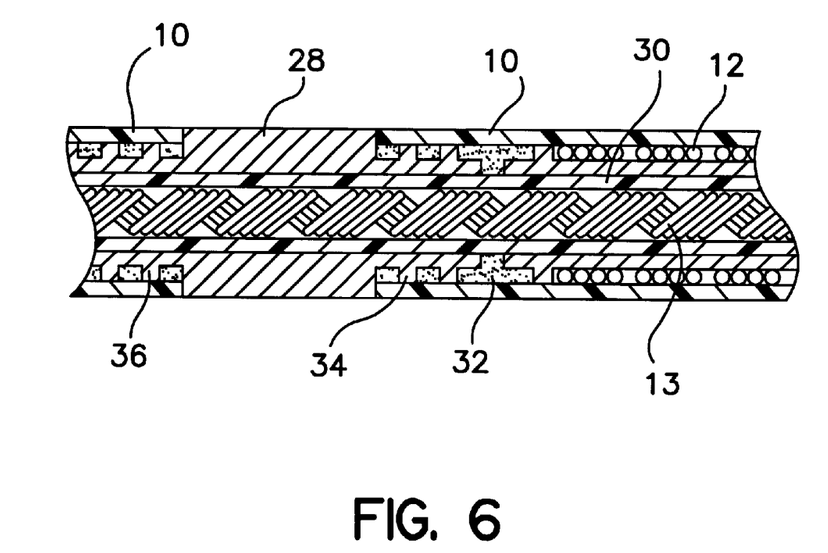
FIG. 6 is a cross-sectional view through a ring electrode or pacing anode appropriate for use in practicing the present invention.

FIG. 6 illustrates a cross-section through the lead of FIG. 1 in the vicinity of the pacing anode or ring electrode 28. Ring electrode 28 may take the form of a platinum electrode provided with a platinum black coating, and may have, for example, a surface area of approximately 36 square millimeters. Electrode 28 is provided with a rearwardly extending electrode shank which includes circumferential ribs 34 and a cross bore 32. Mounted to the proximal end of the electrode shank is a coiled conductor 12 which is welded to the electrode shank. Also visible in this view is an internal insulative sleeve 30 surrounding a second coiled conductor 13 which is in turn coupled to tip electrode 24. Areas between the outwardly extending ribs 32 and 34 and the outer insulative sheath 10 of the lead are filled with adhesive in order to interconnect the sheath with the ring electrode and to provide a fluid seal. The backfield adhesive also extends through the cross bore 32 in order to further interlock the various components of the lead.

In practicing the present invention, ring electrode 28 is first fabricated and coated with platinum black and the lead is thereafter assembled. Prior to packaging, ring electrode 28 may be plasma cleaned according to the method described in conjunction with FIG. 2 and the electrode thereafter may optionally be provided with a steroid coating.

Figure 7:
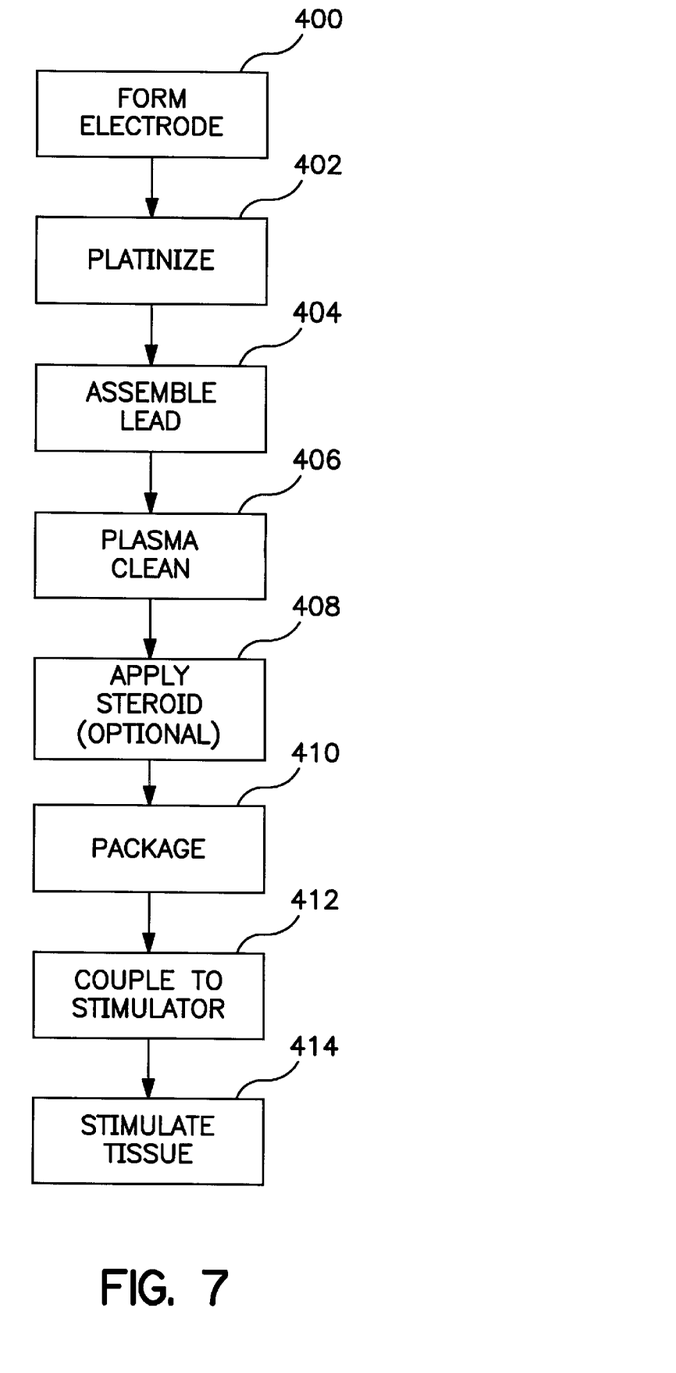
FIG. 7 is a functional flow chart setting forth the method of practicing the present invention.

FIG. 7 is a functional flow chart illustrating the overall process steps employed in practicing the present invention.

As discussed above, the electrode is first formed at 400, and thereafter provided with a coating of platinum black according to the method cited in the above cited Bornzin '492 patent or provided with another high surface area coating, preferably having micron or sub-micron sized surface features at 402. The lead is assembled at 404 including the step of coupling the electrode to an insulated conductor. After assembly of the lead, the electrode or electrodes on the lead may be plasma cleaned at 406 according to the procedure discussed above in conjunction with FIG. 2. If the lead is a steroid eluting lead, the electrode may optionally thereafter be provided with a steroid coating at 408, followed by packaging and sterilization at 410. The lead so produced is now ready to be employed to stimulate a patient's body tissue by coupling the lead to a stimulator at 412 and thereafter applying stimulation pulses to the patient's tissue at 414.

Figure 8:
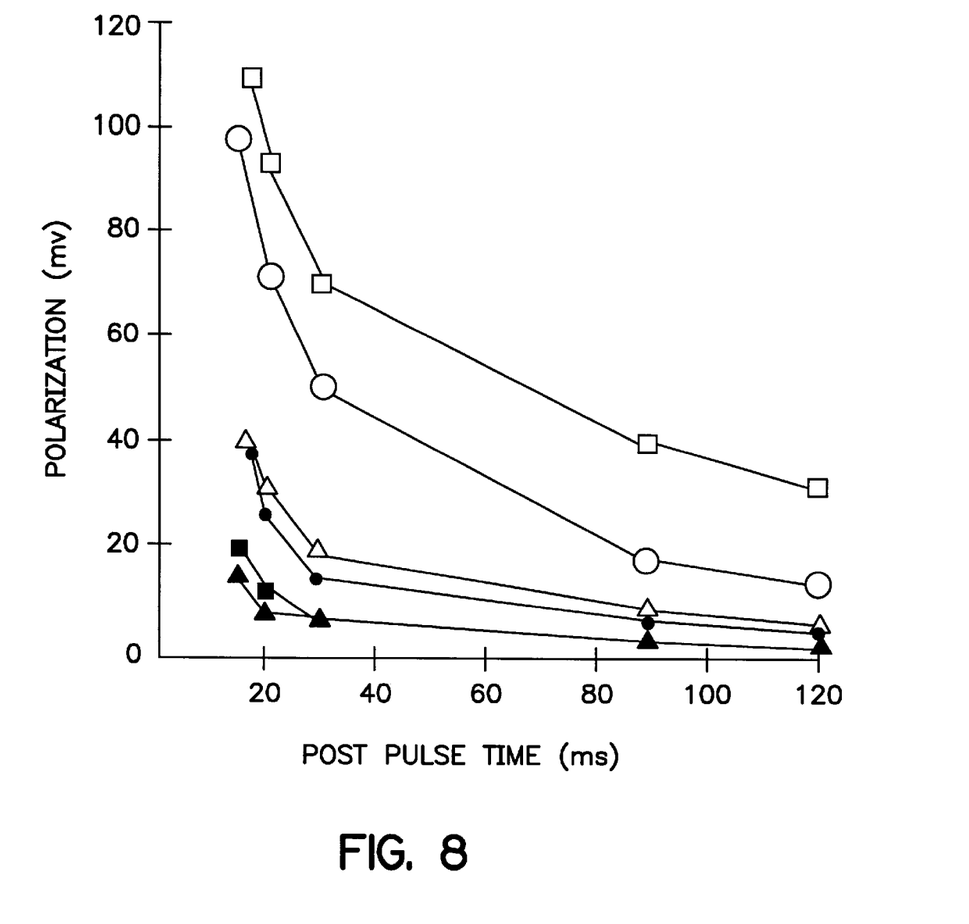
FIG. 8 is a graph illustrating improvements in polarization behavior as a result of the present invention as applied to platinum black coated electrodes.

FIG. 8 illustrates the beneficial effects of a plasma cleaning step according to the present invention. For purposes of FIG. 8, it should be understood that the leads employed for generating the results of FIG. 8 were endocardial pacing leads having distal electrodes or pacing cathodes generally as illustrated in FIG. 2, having a macroscopic geometric surface area of approximately 6 square millimeters and having platinum ring shaped pacing anodes having a surface area of approximately 36 square millimeters. In the chart of FIG. 8, the open squares indicate post pulse polarization levels for such a lead as measured between the electrodes, in canine whole blood, in the case in which the lead has a polished pacing anode not provided with a platinum black coating,. The data points indicated by open circles correspond to the post pulse polarization levels of the same lead as tested in saline solution.

The data points indicated by open triangles correspond to leads of the same type, in which the pacing anode or ring electrode is provided with a platinum black coating but not plasma cleaned, as tested in canine whole blood. The data points indicated by filled circles correspond to the same leads (platinum black coated pacing anodes, not plasma cleaned) as tested in saline solution.

The lower two traces having data points illustrated by filled squares and filled triangles, respectively, indicate the post pulse polarization levels of the same lead type, but having pacing anodes provided with a platinum black coatings and plasma cleaned following assembly of the leads. In the context of this type of lead, the data points indicated by solid squares correspond to post pulse polarization levels in whole canine blood, while the data points indicated by solid triangles correspond to post pulse polarization levels as tested in saline. From approximately 35 milliseconds post pulse, the polarization levels were identical in saline and whole canine blood. All pacing pulses delivered in all cases were 4 volt, 1 millisecond pulses As illustrated in the chart of FIG. 8, provision of a high surface area coating having features in the micron to sub-micron range such as platinum black does indeed provide for a reduced post pulse polarization level. However, the post pulse polarization levels can be even further reduced by the simple expedient of plasma cleaning the electrode, following application of the high surface area coating.

Figure 9:
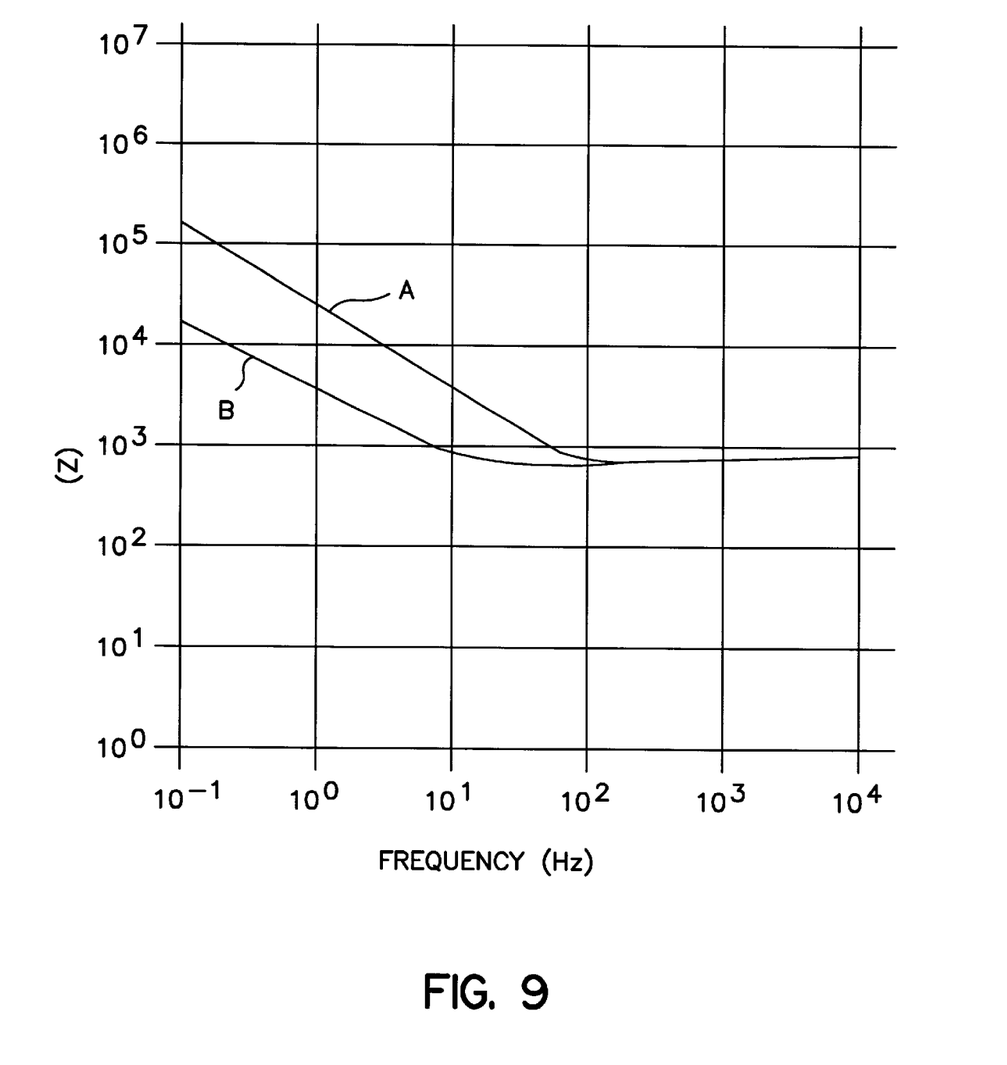
FIG. 9 is a graph illustrating changes in electrode impedance as a result of the present invention as applied to platinum black coated electrodes.

FIG. 9 is a graph illustrating the impedance spectrum of an 11 square millimeter platinum disk with a platinum black coating, with and without plasma cleaning after application of the coating. The upper tracing "A" indicates the impedance spectrum of such a disk absent plasma cleaning. The lower trace "B" indicates the impedance spectrum of such a disk, after plasma cleaning. The decreased impedance at lower frequencies is consistent with improved post pulse polarization performance.

Figure 10:
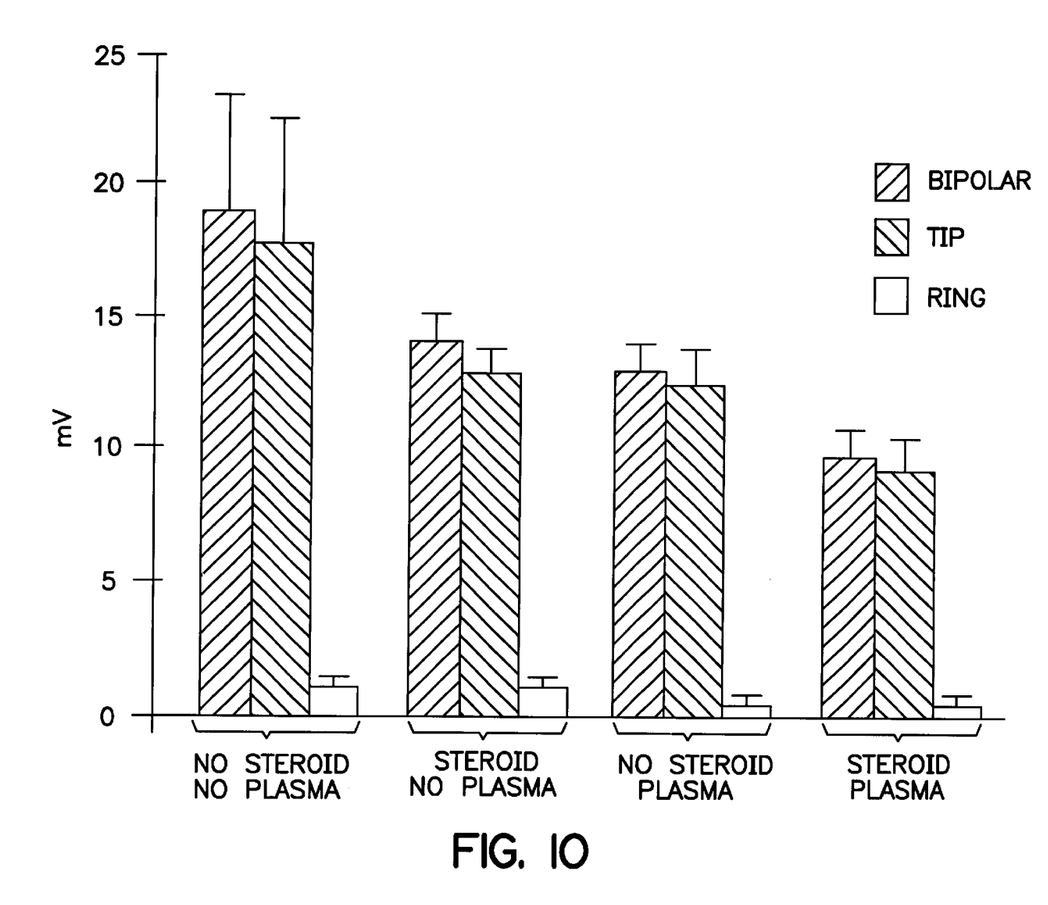
FIG. 10 is a graph illustrating improvements in polarization behavior in electrodes as a result of the present invention as applied to ruthenium oxide coated electrodes.

FIG. 10 is a graph illustrating in-vitro post pulse polarization performance of a lead with a 1.6 square millimeter geometric surface area exposed electrode portion as shown in FIG. 5 in conjunction with a 36 square millimeter geometric surface area pacing anode generally as illustrated in FIG. 6. Both electrodes are provided with a coating of ruthenium oxide, and testing is accomplished employing a 4 volt/1 millisecond pacing pulse. Results are illustrated in which polarization levels of the lead as measured in a bipolar fashion as well as measured at the electrodes individually. The illustrated measurements of post pulse polarization levels were taken at 16 milliseconds after delivery of the pulse, following the end of the passive recharge period of the cardiac pacemaker employed to deliver the pulses. As illustrated, cleaning of the coated electrodes provides for improved post pulse polarization levels both with and without application of steroid.

As noted above, it is believed that the present invention is useful generally in conjunction with high surface area coatings having micron and sub-micron sized surface features. However, it should be understood that the magnitude of the benefit provided by plasma cleaning of the high surface area coating is expected to vary substantially from coating to coating. For example, preliminary testing by the inventors suggests that only a slight improvement in post pulse polarization characteristics may be available attributable to plasma cleaning of titanium nitride coated electrodes.

In conjunction with the above disclosure, we claim:

1. A method of fabricating an implantable stimulation lead, having a conductor and an electrode member, comprising:

coating a lead with a coating of a high surface area, the coating having micron or sub-micron surface features; and plasma cleaning the electrode member.

2. A method of fabricating an implantable stimulation lead, comprising:

coating a conductive electrode member with a coating of a high surface area coating having micron or sub-micron surface features;

coupling the electrode member to an insulated conductor; and plasma cleaning the electrode member.

3. A method according to claim 2 further comprising:

after the cleaning step, applying steroid to the electrode member.

4. A method according to claim 2 wherein the coating step comprises coating the electrode member with platinum black.

5. A method according to claim 2 wherein the coating step comprises coating the electrode member with ruthenium oxide.

6. A method according to claim 2 wherein the coating step comprises coating the electrode member with a metal oxide or metal nitride.

\* \* \* \* \*